US008315439B2

(12) United States Patent
Thomet

(10) Patent No.: US 8,315,439 B2
(45) Date of Patent: Nov. 20, 2012

(54) VISION CORRECTION AID SYSTEM

(75) Inventor: Pascal Thomet, Paris (FR)

(73) Assignee: Interactif Visuel Systeme (IVS), Paris (FR)

( * ) Notice: Subject to any disclaimer, the term of this patent is extended or adjusted under 35 U.S.C. 154(b) by 884 days.

(21) Appl. No.: 12/084,011

(22) PCT Filed: Oct. 23, 2006

(86) PCT No.: PCT/EP2006/067667
§ 371 (c)(1),
(2), (4) Date: Apr. 20, 2009

(87) PCT Pub. No.: WO2007/045694
PCT Pub. Date: Apr. 26, 2007

(65) Prior Publication Data
US 2009/0214086 A1    Aug. 27, 2009

(30) Foreign Application Priority Data
Oct. 21, 2005  (FR) ..................................... 05 10778

(51) Int. Cl.
*G06K 9/00*  (2006.01)
*H04N 9/47*  (2006.01)
(52) U.S. Cl. .......................................... 382/117; 348/78
(58) Field of Classification Search .................. 382/103, 382/117; 348/78; 351/167, 169, 173, 176, 351/177, 178, 206, 209, 239.242, 243; 700/637; 359/600, 642, 643
See application file for complete search history.

(56) References Cited
U.S. PATENT DOCUMENTS
5,167,074 A * 12/1992 Weiss .............................. 33/200
5,984,473 A * 11/1999 Livnat ....................... 351/159.42
6,286,957 B1 * 9/2001 Livnat ............................ 351/204
2005/0195362 A1   9/2005 Brunk FOREIGN PATENT DOCUMENTS
EP          1038495 A     9/2000
WO      WO-01/84222 A    11/2001
WO   WO-2005/071468 A    8/2005

OTHER PUBLICATIONS
Anonymous: "The Measurement of Each Individuals Own Visual Behavior" Varilux IPSEO Vision Print System White Paper, [Online] XP002447206 Retrieved from the internet: URL:http://www.varilux.com/Varilux/PDFs/research_%20VariluxIpseowhitepaper.pds> 25 pages.

* cited by examiner

*Primary Examiner* — Abolfazl Tabatabai
(74) *Attorney, Agent, or Firm* — Blakely, Sokoloff, Taylor & Zafman

(57) ABSTRACT

The invention relates to a system that is used to aid in determining vision correction. The inventive system is characterised in that it combines: a camera which can take animated images of the subject's face along a determined visual axis; a display device which represents the images taken by the camera; an accessory which can be worn by the subject in a fixed manner on the head and which bears a plurality of visual reference marks; means which form the visual reference mark (s) and which can cover at least two determined regions in relation to the camera; and image-analysis means which can analyze the position of the visual reference marks in the images taken by the camera and deduce therefrom the position and spatial orientation of the accessory and, consequently, the subject's head when the subject is looking at a visual target, in order to ascertain information relating to the visual behaviour of the subject when the subject moves the direction in which he/she is looking.

17 Claims, 2 Drawing Sheets

VISION CORRECTION AID SYSTEM

The present patent application is a non-provisional application of International Application No. PCT/EP 2006/067667, filed Oct. 23, 2006.

The present invention generally concerns the analysis of a person's habitual vision movements, for the purpose of optimizing the optical characteristics of corrective lenses, or ophthalmic lenses, that such person needs to wear.

Numerous systems are already known that are intended to optimize the position of the lenses in a frame with respect to the relative position of the wearer's eye pupils and the frame. For this purpose, fixed or animated images of the person's face wearing the frame are taken by camera, and eye position and the positioning of the frame are detected.

In particular, document FR-2860887A on behalf of the applicant discloses a system in which, from a series of animated images of the wearer's face moving in front of a fixed camera, a reference image is determined in which the face is best lined up with the camera, so as to have the best definition of the relative position of the eyes and frame.

Other systems, for example, set out to simulate different forms of frames, by superimposing a real image of the person's face over a virtual image of the frame.

In parallel, some manufacturers of ophthalmic lenses are currently seeking to optimize the design of these lenses, in particular for so-called multifocal lenses, by examining the habitual movements of the person during changes in eye movement.

For example, when reading, a person may follow a line of print by moving the eyes rather more than the head, or on the contrary may move the head rather more than the eyes.

These habitual movements of the person advantageously determine the design of lenses, and in particular the width of their portions for distance vision and near vision.

One item of equipment available on the market to give a first indication of habitual optical movements appears to comprise an accessory worn by a person above the eyes, and provided with active reference marks and with a box having wireless transmitting and receiving means which, on the basis of signals sent towards said reference marks and returned by the latter, are able to determine the position of the wearer's head when such person looks at fixed points laterally staggered on the left and right sides.

The system can roughly deduce whether or not the person has a tendency to move the eyes or rather more has a tendency to move the head during side eye movements.

The present invention sets out to propose a system which can be used to determine a person's eye movement habits whilst maintaining the advantages of video technology in particular for the optimizing of lens positioning in a frame, or to enable persons to see themselves with different types of virtual frames superimposed over the real image of their face by means of computer image technology or other, etc..

For this purpose, the invention proposes a system to assist the determination of eyesight correction, characterized in that it comprises in combination:
   a camera able to take animated pictures of the person's face along a determined viewing line,
   a display device to display the images taken by the camera,
   an accessory able to be fixedly worn on the person's head and having a plurality of visual reference marks,
   means forming visual target(s) able to cover at least two regions determined in relation to the camera,
   image analysis means capable of analyzing the position of the visual reference marks in the images taken by the camera, and to deduce therefrom the position and orientation in space of the accessory, and hence of the person's head, when such person looks towards a visual target, to infer data on the sight habits of the person during visual eye movements.

Some preferred but non-limiting aspects of this system are the following:
   the means forming visual target(s) comprise two localized visual targets on the left and right of a vertical plane passing through the axis of the camera, respectively,
   the means forming visual target(s) comprise at least one generally horizontal line,
   the means forming visual target(s) comprise a printed document,
   a light source is associated with or integrated in the printed document,
   the means forming visual target(s) comprise two targets spaced vertically away from each other,
   one of the two vertically spaced apart targets is positioned substantially at camera height, and the other is positioned below the camera,
   the system comprises means to move at least one target,
   the system comprises means to move the camera vertically and to orientate its viewing line at a low angle,
   the system comprises means to move at least one target vertically with the camera,
   the image analysis means are able to determine turning of the head when the eyes move between targets, and the system comprises calculation means to deduce data on head turning and the position of said targets relative to the camera, and data on eye movements thereby obtaining the distribution between the head movement and eye movement of the person during said eye movement,
   the image analysis means and the calculation means are able to produce such data statically when the wearer looks towards a target,
   the image analysis means and the calculation means are able to produce said data dynamically during eye movement of the wearer,
   the image analysis means and calculation means are able to produce said data dynamically when the wearer's eyes come to set on the target,
   the system comprises means to calculate a mean position between several positions of the accessory, measured in one same situation,
   the image analysis means are also capable of determining a reference position of the wearer's head in which the accessory takes up a generally symmetrical position relative to a vertical plane parallel to the viewing line of the camera,
   the visual reference marks of the accessory are localized areas of well-determined color, and in that the image analysis means comprise calorimetric filtering means.

Other aspects, purposes and advantages of the present invention will become better apparent on reading the following detailed description of preferred embodiments thereof given as non-limiting examples, with reference to the appended drawings in which.

With reference to the drawings, a system to assist determination of sight correction is shown, with a view to designing spectacle lenses or ophthalmic lenses. This system comprises a frame 10 whose upper region includes a color filming camera 12 and a color display screen 14 e.g. a cathode ray or liquid crystal display.

Figure 1:
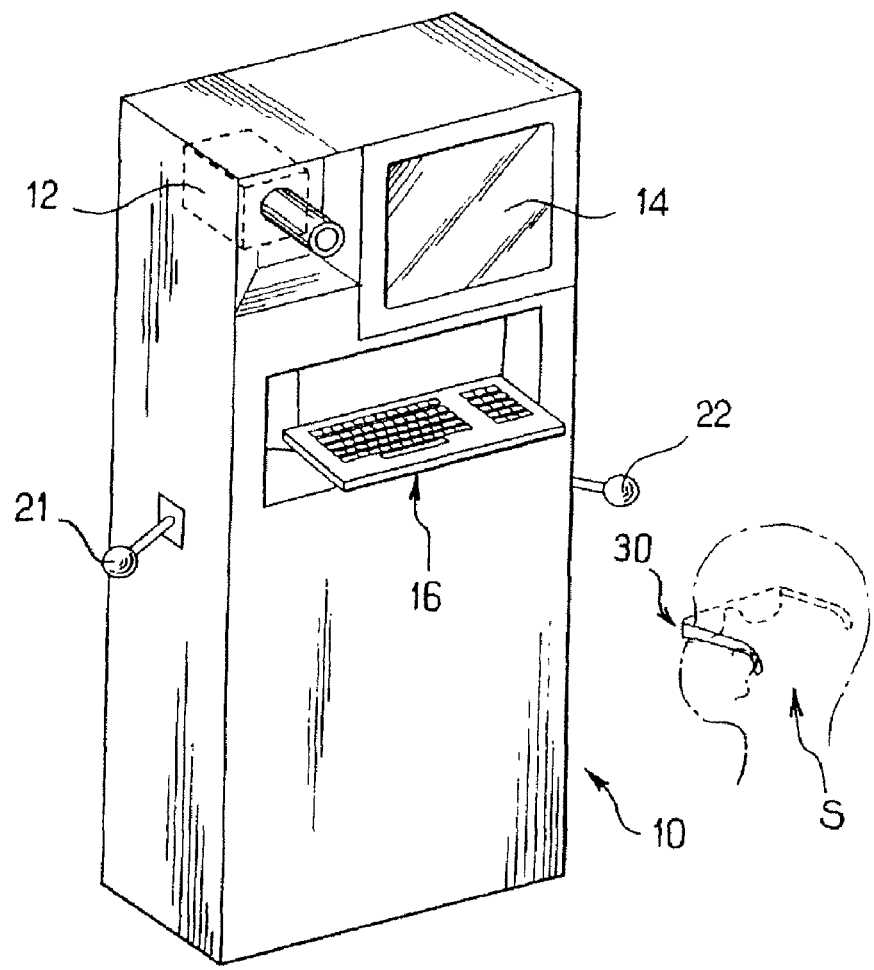
FIG. 1 is a perspective schematic view of a system according to the invention.
Figure 2:
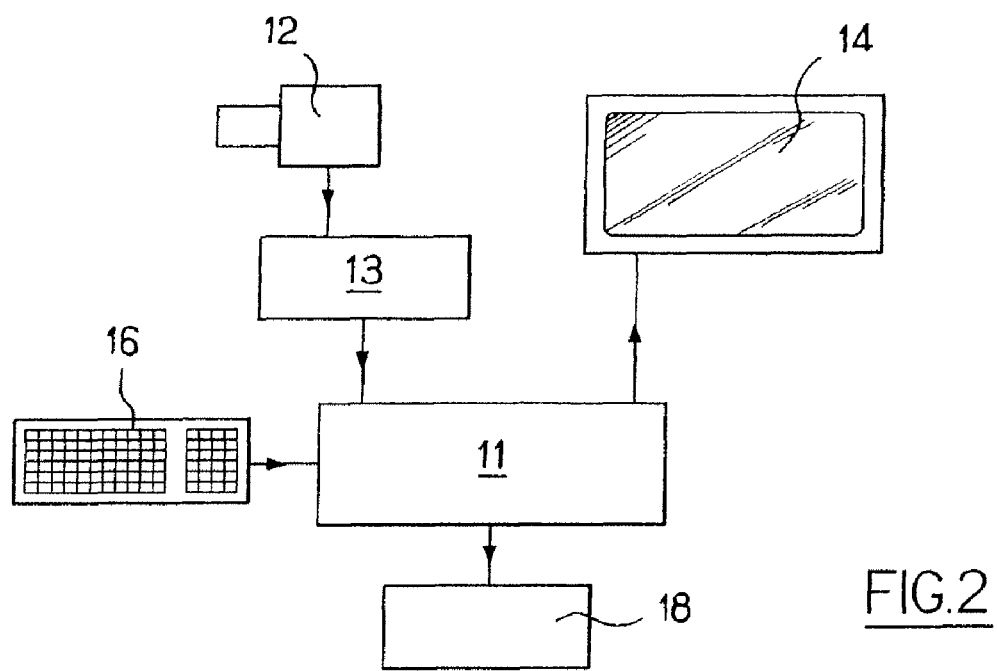
FIG. 2 is a block diagram of the different essential components of the system of the invention.

FIG. 2 particularly shows that the camera 12 is linked to a central unit 11 via a video acquisition card 13 in manner known per se. The central unit 11 pilots a screen 14 via a video output circuit, not shown, also known per se.

A keypad 16 and any other entry device such as a mouse etc., not illustrated, is used to command the system as will be detailed further on.

The system also comprises two visual targets 21, 22 positioned laterally either side of the frame which are intended to be viewed by a person on instructions given by an operator as will be detailed below. These targets may be regions that are visually clearly identifiable and located in well determined positions or which can be determined relative to the viewing line of the camera 12.

Figure 3:
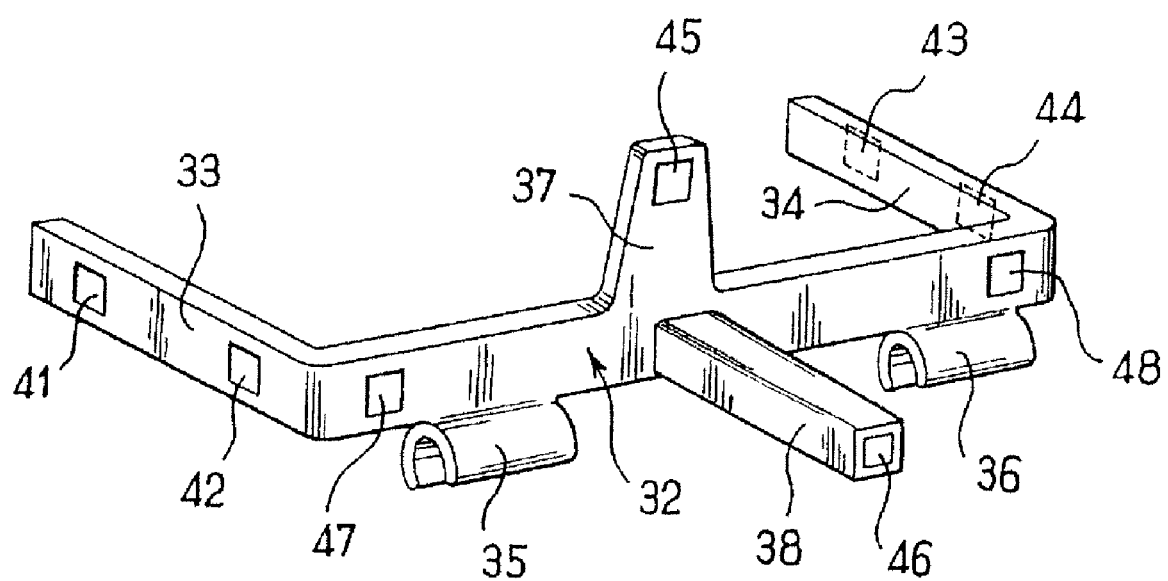
FIG. 3 is a perspective view of an accessory used in the system of the invention.

The system also comprises an accessory intended to be secured to the head of the individual S as illustrated in detail FIG. 3.

This accessory 30 made in a transparent plastic material for example, comprises a main body 32 that is horizontally elongate with two side arms 33, 34 that are also horizontal extending substantially at right angles towards the rear relative to the main body. The main body 32, along its lower edge, comprises two small clips 35, 36 intended to hook along the upper edges of two spectacle lenses (or on a frame) worn by the person S, the arms 33, 34 possibly also carrying arrangements, not illustrated, which fit onto the arms of the frame.

In this manner, once the person has donned spectacles (corrective or optically neutral, or even a bare frame) in very stable position, said accessory 30 assumes a well-defined position relative to the individual's head.

As illustrated FIG. 3, the accessory 30 comprises a certain number of markers or visual references, in this case eight square areas 41 to 46 of well-identified color e.g. bright green and of well-defined wavelength, two visual references 41 42 being located at well-defined, spaced apart locations on one of the arms 33, 34, two others 43, 44 arranged symmetrically on the other arm, and finally four others 45 to 48 positioned on the main body.

More precisely, with respect to these latter reference marks, the main body 32 of the accessory comprises an upward projecting part 37, in the upper region of which there is a reference mark 45, and a forwardly projecting part 38 at whose free end there is a reference mark 46. The two final marks 47 and 48 lie on the left and right close to the starting point of the arms 33 and 34.

Evidently, any other arrangement of the markers, which may optionally be more numerous, can be used notably in relation to the types of movements to be given priority analysis, the desired accuracy and any ambiguities to be solved when the markers are too few in number and/or their spacing is too uniform.

The central unit 11 preferably includes analysis means, via suitable programming, to analyze the images taken by the camera 12 and intended:
 to identify, on the images taken by the camera, the different visual reference marks (bearing in mind that the reference marks of one of the side arms or of the two arms may not be seen by the camera); this identification is made in particular by filtering the image on the wavelength corresponding to the color of the visual reference marks;
 to determine the coordinates of the centers of each of the visible visual marks relative to an image reference system;
 to calculate, in relation to said coordinates, the position and incline of the head preferably in the six possible degrees of freedom, so as to integrate all possible head movements.

Preferably, these calculations are made in relation to an initially determined reference position (<<in line position>>) e.g. in accordance with document FR-2860887A on behalf of the applicant, the suitable height of the viewing line of the camera 12 having been previously adjusted manually or automatically. This is obtained preferably by identifying the head position in which the accessory takes up a generally symmetrical position relative to a vertical plane parallel to the viewing line of the camera.

The described system is therefore implemented as follows.

Once the reference position of the face is determined as indicated above, the positions of the visual reference marks of the accessory in this reference position are stored in memory. The person is then requested to look at the left visual target and then the right visual target. Each time an instruction is given to the system e.g. using a key on the keypad 16 so that the image analysis means calculate the current position of the individual's head from the current position of the visual reference marks lying in the image.

Evidently, the requests given to the person may vary widely, to analyze habits of movement. In particular, the individual may be requested to look at the left and right targets several times alternately. The system processes the sequence of images taken by the camera in real or deferred time during these movements. It can, for example, calculate a mean position of the head (which will be used as reference position) during these movements, a mean position of the head when looking at the left target 21, and finally a mean position of the head when looking at the right target 22.

More precisely the image processing means, in the image taken at the time of the above-cited instruction, identify the coordinates of the visible visual reference marks, and chiefly of the four visual marks 45-48 which are more likely to face the camera, and it will easily be appreciated that by means of the specific arrangement of the visual marks, and using algorithms chiefly based on trigonometric geometry, the central unit is able to determine changes in head positions and incline relative to the reference position in the six degrees of freedom.

The variations in viewing angle when observing the left target and when observing the right target are known through the fact that the system firstly knows the position of said targets, and secondly by means of the accessory 30 knows the position of the person's head. The system is therefore capable of determining data on the relative importance of head movement when changing vision from one target to another, and subsequently to infer the relative importance of eye movement. This data is delivered to an output 18 (display, print-out, lens manufacturing equipment, etc.).

In another embodiment of the invention, which can be accumulated with the above embodiment, the system may be designed to measure the downward tilting of the head, in particular when the person changes from distance vision (looking horizontally or substantially horizontally) to near vision (looking downwards), once or several times alternately as in the foregoing case.

In this case, the system advantageously comprises a first visual target positioned substantially at the height of the camera (e.g. fixed to said camera) and a second target positioned at a certain distance below the camera e.g. a few dozen centimeters away. This second target could be either an open book or a sheet of paper with characters which the person is requested to read. In this case, it is advantageous to associate or integrate a light source with this target e.g. a small battery-powered reflector, this source being directed towards the person's face so as to obtain an image of satisfactory quality in particular to detect, by image analysis, the position of the person's eye pupils by means of corneal reflection, and optionally to facilitate the position of the accessory 30 and hence of the person's head.

Advantageously, manual or motorized means are provided to move the camera and the targets, independently of each other or together, so that the camera and the first target lie substantially at eye height, and the second target lies at the desired distance below the camera.

Further preferably, provision may be made for the second target (typically characters to be read) to lie behind glass or a semi-transparent mirror belonging to the frame 10, tilted at an angle suitable for reading, the assembly moving vertically together with the camera.

According to one variant of this other embodiment, provision may be made for the second target to be simply a book or document placed in the person's hands as indicated above, the person then taking up a natural reading position. The exact position of the second target is then not accurately known by the system (no determined position relative to the camera), but any means may be provided (visual references on the book and/or frame) to give the best possible determined position to achieve reliable analysis of habitual optical movements.

In this case, it is advantageous for the system to lower the camera and to orientate it for low-angle filming so that, optionally in association with the above-described light source, a better image of the person's face can be obtained, in particular better dynamic analysis and better discrimination between eye movement and head movement when arriving at reading position.

According to a further embodiment, the system can be designed to analyze the person's habitual movements when reading a document of fixed size. In this case, it is not the visual targets 21 and 22 of the first embodiment which are used, but a document (e.g. an A4 format sheet) on which text is printed.

In this case, it is the entirety of the text which forms the different visual targets, the (geometric) size of the text and its position relative to the camera, which are at least approximately known, being used to determine the relative importance of head movement and eye movement when reading, by means of the above-described image analysis means.

More precisely, in this case the system analyzes a series of images taken during the reading phase, to carry out the above-mentioned determination in dynamic fashion, in real time or deferred time depending in particular on the calculation power of the system.

As in the preceding example, the target here consisting of the written document may belong to the system, and then preferably lies behind a glass inside the frame and is able to move upwards relative to the camera, or it may simply be held in the person's hands.

Here again, it is preferable for the camera to film at a low angle to obtain an image that allows most reliable image analysis Evidently, numerous variants can be made to the invention.

First, the physical arrangement of the different components of the system can vary widely from the described arrangement. For example, by means of return optical systems with semi-transparent mirrors, the viewing line of the camera 12 and the axis of the screen (the normal to the screen at its centre) 14 can be caused to merge or lie close to each other so that the person is filmed from the front when such person faces the screen. The camera 12 can, if necessary, be motorized in vertical movement but also in side movement, at an angle, for magnification, etc.

It is also possible to add to the accessory any other visual reference arrangement, of identical or different colors, which can be used by simple image analysis to determine the position and orientation in the six degrees of freedom of said accessory 30 and hence of the person's head Additionally, it is possible with the system of the invention to conduct dynamic analysis of habitual optical movements. In particular, the person may be requested to view a given pathway, typically a horizontal line (line of writing or mere reference mark) at greater or lesser speed, and through analysis of the images successively taken by the camera, to determine dynamically how the head and eyes move and thereby obtain more detailed information on the manner in which a multifocal lens must be designed. This process can be carried out both for near vision and for distance vision.

Finally, the invention can be combined with any image processing which can be used in particular to superimpose various computer-generated images over the person's face which represent different frame models, to reprocess the area taken up by the accessory 30 so that it is invisible in the delivered image (in particular re-processing of visual references whose strongly marked coloring may be undesirable on the screen, etc.

The invention claimed is:

1. System to assist determination of eyesight correction, characterized in that it comprises in combination:
   a camera able to take animated images of person's face along a determined viewing line,
   a display device to display the images taken by the camera,
   an accessory able to be worn fixedly on the person's head and carrying a plurality of visual reference marks,
   means forming visual target(s) able to cover at least two determined regions relative to the camera,
   image analysis means capable of analyzing the position of the visual references in the images taken by the camera and subsequently to deduce the position and orientation in space of the accessory, and hence of the person's head, when such person looks towards a visual target, to infer data on habitual vision movements of the person during visual eye movements.

2. System according to claim 1, wherein the means forming visual target(s) comprise two localized visual targets positioned on the left and right of a vertical plane passing through the viewing line of the camera, respectively.

3. System according to claim 2, wherein the means forming visual target(s) comprise a printed document.

4. System according to claim 3, wherein a light source is associated with or integrated in the printed document.

5. System according to claim 1 or 2, wherein the means forming visual target(s) comprise at least one generally horizontal line.

6. System according to claim 1, wherein the means forming visual target(s) comprise two targets vertically spaced apart.

7. System according to claim 6, wherein one of the vertically spaced apart targets is positioned substantially at camera height, and the other is positioned below the camera.

8. System according to claim 1 or claim 7, further comprising means to move at least one target.

9. System according to claim 8, further comprising means to move the at least one target vertically with the camera.

10. System according to claim 1, further comprising means to move the camera vertically and to orientate its viewing line at a low angle.

11. System according to claim 1, wherein the image analysis means are able to determine turning of the head when moving eyes from one target to another, and further comprising calculation means to deduce information on head turning movements and on the position of said targets relative to the camera, data on eye movements, and thereby obtain a distribution between head movement and eye movement of the person during said eye movement.

12. System according to claim 11, wherein the image analysis means and the calculation means are able to produce said data statically when the person looks at a target.

13. System according to claim 12, further comprising means to calculate a mean between several positions of the accessory measured in one same situation.

14. System according to claim 11, wherein the image analysis means and the calculation means are able to produce said data dynamically during the person's changing eye movements.

15. System according to claim 14, wherein the image analysis means and the calculation means are able to produce said data dynamically when the person comes to moves eyes towards a target.

16. System according to claim 1, wherein the image analysis means are also capable of determining a reference position of the person's head, in which the accessory assumes a generally symmetrical position relative to a vertical plane parallel to the viewing line of the camera.

17. System according to claim 1, wherein the visual references of the accessory are localized areas of well-determined color, and the image analysis means comprise calorimetric filtering means.

* * * * *